(12) United States Patent
Nollert et al.

(10) Patent No.: US 12,714,558 B2
(45) Date of Patent: Aug. 25, 2026

(54) CATHETER AND ASSEMBLY WITH A POSITIONAL IDENTIFIER FOR A MEDICAL IMPLANT

(71) Applicant: BIOTRONIK AG, Buelach (CH)

(72) Inventors: Georg Nollert, Strasslach (DE); Tobias Kissling, Bern (CH)

(73) Assignee: BIOTRONIK AG, Buelach (CH)

( * ) Notice: Subject to any disclaimer, the term of this patent is extended or adjusted under 35 U.S.C. 154(b) by 996 days.

(21) Appl. No.: 17/785,149

(22) PCT Filed: Jan. 8, 2021

(86) PCT No.: PCT/EP2021/050284
§ 371 (c)(1), (2) Date: Jun. 14, 2022

(87) PCT Pub. No.: WO2021/144203
PCT Pub. Date: Jul. 22, 2021

(65) Prior Publication Data

US 2023/0012858 A1 Jan. 19, 2023

(30) Foreign Application Priority Data

Jan. 16, 2020 (EP) .................................... 20152124

(51) Int. Cl.
*A61F 2/24* (2006.01)

(52) U.S. Cl.
CPC .... *A61F 2/2427* (2013.01); *A61F 2250/0032* (2013.01)

(58) Field of Classification Search
CPC ............. A61F 2/966; A61F 2/95–2/97; A61M 25/0108; A61B 2017/00292–2017/00336
See application file for complete search history.

(56) References Cited

U.S. PATENT DOCUMENTS

| | | | | | |
|---|---|---|---|---|---|
| 5,405,380 | A * | 4/1995 | Gianotti | A61F 2/88 | 623/1.34 |
| 5,534,007 | A * | 7/1996 | St. Germain | A61F 2/95 | 606/198 |
| 5,709,703 | A * | 1/1998 | Lukic | A61F 2/95 | 606/198 |
| 5,733,325 | A * | 3/1998 | Robinson | A61F 2/07 | 623/1.11 |
| 5,824,041 | A * | 10/1998 | Lenker | A61F 2/91 | 606/195 |

(Continued)

OTHER PUBLICATIONS

International Search Report from the corresponding International Patent Application No. PCT/EP2021/050284, dated Jan. 8, 2021.

(Continued)

*Primary Examiner* — Alvin J Stewart
(74) *Attorney, Agent, or Firm* — Greer, Burns & Crain, Ltd.; Steven P. Fallon

(57) ABSTRACT

A catheter includes a positional identifier/marker at a tip section for a medical implant that needs to be aligned rotationally and/or axially and/or in terms of tilting in a human or animal body. The positional identifier is shaped and/or arranged such that a rotational orientation and/or an axial orientation and/or a tilted orientation of the tip section relative to the surrounding tissue is discernable from the position and/or orientation of the positional identifier.

20 Claims, 9 Drawing Sheets

(56) References Cited

U.S. PATENT DOCUMENTS 6,024,763 A 2/2000 Lenker et al.
6,285,903 B1 * 9/2001 Rosenthal ......... A61M 25/0108 600/433
6,395,017 B1 * 5/2002 Dwyer .................... A61F 2/966 623/1.11
6,613,075 B1 * 9/2003 Healy ..................... A61F 2/966 606/108
6,676,693 B1 * 1/2004 Belding .................... A61F 2/95 606/108
6,776,791 B1 * 8/2004 Stallings ................... A61F 2/95 623/1.11
7,258,696 B2 * 8/2007 Rabkin ................ A61B 17/221 606/191
7,824,443 B2 * 11/2010 Salahieh ............... A61F 2/2439 623/2.11
9,320,503 B2 * 4/2016 Bolduc ............ A61B 17/00234
9,439,795 B2 * 9/2016 Wang .................... A61F 2/2418
9,510,947 B2 * 12/2016 Straubinger .......... A61F 2/2436
10,028,854 B2 * 7/2018 Tatalovich .............. A61F 2/962
2014/0051968 A1 * 2/2014 Isham ...................... A61N 5/10 600/407
2014/0371718 A1 * 12/2014 Alvarez .............. A61M 25/003 604/164.11
2015/0165170 A1 * 6/2015 Beasley ............ A61M 25/0108 604/103.1
2018/0221147 A1 8/2018 Ganesan et al.
2018/0344980 A1 * 12/2018 Contreras ......... A61M 25/0147
2019/0192275 A1 6/2019 Kim et al.
2020/0222215 A1 * 7/2020 Woerne ................... A61F 2/958
2022/0151763 A1 * 5/2022 Klausmann ............. A61F 2/852

OTHER PUBLICATIONS

Chinese Office Action (and translation) from the corresponding Chinese Patent Application No. 202180008656.6, dated Aug. 30, 2024.

* cited by examiner

CATHETER AND ASSEMBLY WITH A POSITIONAL IDENTIFIER FOR A MEDICAL IMPLANT

PRIORITY CLAIM

This application is a 35 U.S.C. 371 US National Phase and claims priority under 35 U.S.C. § 119, 35 U.S.C. 365(b) and all applicable statutes and treaties from prior PCT Application PCT/EP2021/050284, which was filed Jan. 8, 2021, which application claimed priority from European Application Serial Number 20152124.2, which was filed Jan. 16, 2020.

FIELD OF THE INVENTION

A field of the invention is catheters for medical implants, such as catheters used to implant artificial heart valves.

BACKGROUND

A common therapy to treat severe aortic valve stenosis (narrowing of the aortic valve) involves implanting an artificial heart valve into the annulus of the native aortic valve. Typically, such artificial heart valves comprise a compressible and expandable frame structure such as a stent that is coupled to valve leaflets or cusps from bovine or porcine pericardium or a synthetic material.

As a less invasive alternative to open heart surgery, transcatheter aortic valve implantation (TAVI) or transcatheter aortic valve replacement (TAVR) or percutaneous aortic valve replacement (PAVR) has become a widely used procedure to implant a replacement heart valve in order to treat aortic valve disease; e.g. aortic stenosis. In this procedure, a catheter harboring the compressed stent with the artificial valve including leaflets and optionally further including a skirt element is advanced through the patient's arterial system via the aorta to its final position in the native valve annulus and expanded; either by actuating a force-expandable means such as a balloon or due to its self-expanding properties such as in case of a conventional nitinol stent.

Since the coronary ostia (the orifices originating from the aorta leading to the coronary arteries) are positioned close to the native aortic valve annulus, they may be obstructed by structures of the stent of the replacement heart valve upon implantation which can, e.g., lead to severe side effects due to impaired blood supply to the coronary arteries.

Some heart valves according to the prior art include windows to be placed above the coronary ostia to avoid such obstruction, and to ensure sufficient blood supply. However, correctly placing such heart valves during the TAVI/TAVR procedure remains difficult.

Heart valves including radiopaque markers indicating the correct rotational orientation with respect to the surrounding tissue have been described in the prior art (cf., e.g., U.S. Pat. Nos. 8,998,981, 9,943,407, WO 2015/006139). However, these radiopaque markers remain in the patient body after implantation, which may lead to health risks depending, e.g., on the nature of the marker.

Furthermore, larger radiopaque markers require space which can result in an increased diameter of the stent in the compressed (crimped) state. Small indicators, in turn, are difficult to be recognized in fluoroscopic images, and thus complicating the orientation procedure. Finally, markers on the stent may be masked by radiopaque structures of the catheter, impairing visibility of the marker itself.

Other solutions according to the prior art include radiopaque indicators on the prosthesis connector (EP 2 651 335, WO 2016/059084) or on a capsule disposed around the heart valve in the catheter (U.S. Pat. Nos. 9,387,106, 10,154,921). However, visibility of these markers in fluoroscopy may be impaired by the metal core of the catheter capsule or outer shaft or by the stent itself.

SUMMARY OF THE INVENTION

A preferred catheter for a medical implant that includes a frame structure that requires a rotational and/or axial and/or tilted alignment in a human or animal body is provided. The catheter includes an inner shaft extending along a longitudinal axis (L), wherein the inner shaft is configured to receive the frame structure such that the frame structure is rotationally fixed to the inner shaft with respect to a rotation around the longitudinal axis (L). A tip section is connected to the inner shaft, wherein the tip section forms a distal end of the catheter, and wherein the tip section is rotationally fixed to the inner shaft with respect to a rotation around the longitudinal axis (L). The tip section includes a positional identifier shaped and/or arranged such that a rotational orientation and/or an axial orientation and/or a tilted orientation of the tip section relative to the surrounding tissue is discernable from the position and/or orientation of the positional identifier.

BRIEF DESCRIPTION OF THE DRAWINGS

The invention is further illustrated by the following examples and figures, from which further embodiments and advantages can be drawn. These examples are meant to illustrate the invention but not to limit its scope.

DETAILED DESCRIPTION OF THE PREFERRED EMBODIMENTS

Figure 1:
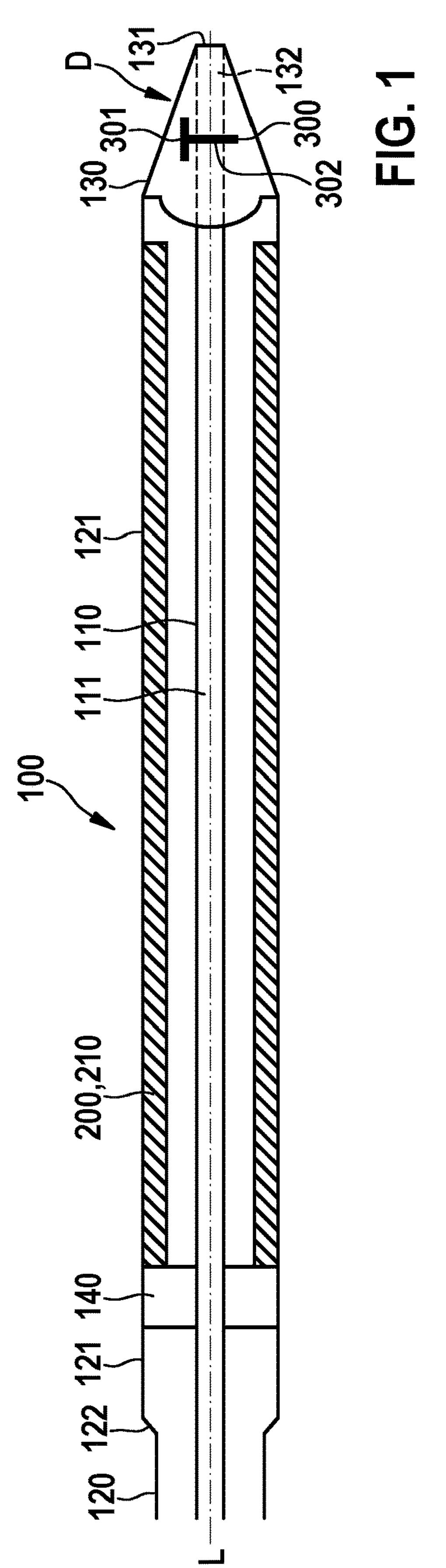
FIG. 1 shows a sectional schematic view of an exemplary catheter according to the present invention.

A preferred catheter for delivery of a medical implant such as a heart valve implant includes a positional identifier. The identifie includes rotational and/or axial orientation and/or optionally indicating a tilting of a frame structure such as a stent of an implant, particularly of an artificial aortic heart valve, before deployment.

The positional identifier of the invention for an adequate delivery of a medical implant is suitable for other implants as an artificial aortic heart valve and other artificial heart valves as well such as mitral valves, tricuspid valves, pulmonal valves, or artificial valves such as venous valves. Particularly, mitral valves also require a correct positioning at the implantation site of a D-shaped annulus.

Thus, with the context of the present invention the expression "medical implant" denotes any suitable kind of a medical implant including some sort of a frame structure and being in need of a general or specific rotational and/or axial and/or tilted alignment in a human or animal body at an implantation site.

Nevertheless, the present invention of a catheter including a positional identifier is predominantly exemplified herein by an artificial heart valve such as an aortic artificial heart valve, but without being limited thereto.

The invention relates to a catheter including a positional identifier for a medical implant that needs to be aligned in terms of its position such as rotationally and/or axially and/or in terms of tilting of the medical implant in a human or animal body and an assembly including the catheter and the medical implant. Particularly, the invention relates to a catheter including the positional identifier for deployment of a heart valve implant such as an aortic heart valve implant that needs to be aligned in terms of its position such rotationally and/or axially and/or in terms of tilting of the heart valve implant in a human or animal body and an assembly including the catheter and the heart valve implant; e.g. aortic heart valve implant.

A first aspect of the invention relates to a catheter for deployment of a heart valve implant such as an aortic heart valve prosthesis in a human or animal body at a native heart valve annulus, the catheter including an inner shaft extending along a longitudinal axis, wherein the inner shaft is configured to receive a frame structure such as a stent portion of the heart valve implant in a radially compressed state, such that the stent portion is rotationally fixed to the inner shaft with respect to a rotation around the longitudinal axis. The catheter further includes a tip section connected to the inner shaft, wherein the tip section forms a distal end of the catheter, and wherein the tip section is rotationally fixed to the inner shaft with respect to a rotation around the longitudinal axis.

According to the invention, the tip section (such as, e.g., a nosecone of a catheter) includes a positional identifier/marker which is configured to be visualized from an outside of the human or animal body, particularly by fluoroscopy, particularly during deployment of the heart valve implant, wherein the marker is shaped and/or arranged such that a rotational orientation of the tip section in respect of a rotation of the catheter and/or the tip section around the longitudinal axis relative to surrounding tissue is discernable from the position and/or orientation of the marker, particularly when viewed from a tip of the tip section in the direction of the longitudinal axis or from a plane arranged perpendicular to the longitudinal axis.

With the context of the present invention, the terms "positional identifier" and "marker" may be used interchangeably, provided that they are configured to be visualized from an outside of the human or animal body, particularly by fluoroscopy, particularly during deployment of a medical implant, and thus they allow for determining the position of a medical implant in terms of a rotation and/or an axial alignment and/or a tilting; e.g. during fluoroscopy.

Alternatively or additionally, according to the invention, the tip section (such as, e.g., a nosecone of a catheter) includes a positional identifier/marker which is configured to be visualized from an outside of the human or animal body, particularly by fluoroscopy, particularly during deployment of the heart valve implant, wherein the positional identifier/marker is shaped and/or arranged such that an axial orientation of the tip section relative to surrounding tissue is discernable from the position and/or orientation of the marker.

Alternatively or additionally, according to the invention, the tip section (such as, e.g., a nosecone of a catheter) includes a positional identifier/marker which is configured to be visualized from an outside of the human or animal body, particularly by fluoroscopy, particularly during deployment of the heart valve implant, wherein the positional identifier/marker is shaped and/or arranged such that a tilted orientation of the tip section relative to surrounding tissue is discernable from the position and/or orientation of the marker.

The positional identifier/marker disposed at the tip section of the catheter allows optimal rotational and/or axial positioning, optionally also in terms of tilting, of the heart valve implant relative to the surrounding anatomy, particularly the native heart valve (e.g. aortic valve) and the coronary ostia. The placement of the positional identifier/marker at the tip section (such as, e.g., a nosecone) of the catheter ensures good visibility of the positional identifier/marker (e.g. under X-ray illumination such as during fluoroscopy), since the positional identifier/marker is spaced away from both the frame structure such as a stent portion of the heart valve implant, and spaced away from a metal capsule commonly placed around the heart valve implant, so that the positional identifier/marker is not covered or shielded by the stent or the capsule.

Within the context of the present specification, the term "deployment" means implanting the heart valve implant, e.g., in the native valve annulus, such that the stent or support structure portion of the heart valve implant expands to anchor the heart valve in the native valve annulus. The skilled artisan hereby readily understands that a heart valve can be also placed at other suitable anatomical sites such as in the vena cava or, e.g., pulmonary veins, if indicated.

In certain embodiments, the catheter further includes a proximal end opposite the distal end.

As used herein, the term "proximal" refers to the direction towards the physician implanting the heart valve, and the term "distal" refers to the direction towards the heart of the patient. Thus, a handle including actuators for controlling the orientation of the catheter is typically positioned at the proximal end of the catheter, and the tip section forms the distal end of the catheter.

The heart valve implant in preferred embodiments is particularly an aortic valve implant, i.e., the heart valve implant is configured to replace the aortic valve (between the left ventricle and the aorta).

The heart valve implant generally includes a compressible and expandable frame structure, e.g., a mesh-like structure composed of interconnected struts forming openings (also termed cells) between the struts, or a wire structure, or a braided wire structure, and so to form a stent or support structure, whereby the stent or support structure is configured to provide a radially oriented (in respect of a longitudinal axis of the stent) outward force to engage native tissue and tightly anchor the heart valve in the tissue. The stent or support structure portion may be self-expanding or mechanically expandable, e.g., balloon-expandable. In particular, the stent or support structure portion may consist of nitinol (a nickel-titanium alloy displaying shape memory and superelasticity or pseudo-elasticity). Furthermore, the heart valve implant includes a plurality of cusps or valve leaflets, particularly from porcine or bovine pericardium or a synthetic material, connected to the stent or support structure portion, replacing the native heart valve.

In the context of the present specification, the term "rotational orientation" designates the orientation of components of the catheter when the catheter is rotated around the longitudinal axis or the rotation of the heart valve prosthesis around the axis of blood flow from inflow to outflow of the prosthesis.

Throughout this specification, "components rotationally fixed to each other with respect to a rotation around an axis" designate components which are mechanically connected to each other such that no rotation between the components around the longitudinal axis may occur.

In certain embodiments, the tip section includes a tip forming the distal end of the tip section. In certain embodiments, the tip section may be a nosecone.

The tip section of the catheter, which may also be termed "nosecone", forms the distal end of the catheter and is particularly configured to allow for an easy, atraumatic navigation over a stiff guidewire (particularly contained in the inner shaft; an inner shaft typically includes a guidewire lumen) even through challenging anatomies. In certain embodiments, the tip section includes a smooth, atraumatic surface. In certain embodiments, the tip section is conical, wherein a diameter of the tip section perpendicular to the longitudinal axis decreases towards the tip (in the distal direction). In certain embodiments, the proximal end of the tip section includes a diameter matching the diameter of a distal end of a capsule. Hereby, the skilled artisan readily understands that a catheter does not necessarily includes a capsule, such as in case of a balloon-expandable catheter.

In certain embodiments, the catheter further includes an outer shaft extending along the longitudinal axis radially outside of the inner shaft, particularly concentrically around the inner shaft. In certain embodiments, the heart valve implant is arrangeable between the inner shaft and the outer shaft, wherein particularly the outer shaft is configured to radially constrain the frame structure such as stent portion, such that the stent portion is kept in the radially compressed state. The outer shaft of the catheter may be movable along the longitudinal axis relative to the inner shaft to deploy the heart valve implant (wherein particularly the outer shaft is moved in the proximal direction relative to the inner shaft) and/or to recapture the heart valve implant (wherein the outer shaft is moved in the distal direction relative to the inner shaft).

In certain embodiments, the outer shaft may be connected to or integrally formed with a capsule for radially constraining the heart valve implant, wherein the heart valve implant is disposed between the inner shaft and the capsule (which is arranged radially outside of the inner shaft). In particular, the capsule is movable along the longitudinal axis relative to the inner shaft to deploy the heart valve implant (moving in the proximal direction) and/or to recapture the heart valve implant (moving in the distal direction). Therein, the outer shaft may be movable together with the capsule relative to the inner shaft to deploy or recapture the heart valve implant.

In certain embodiments, the inner shaft includes a guidewire lumen for receiving a guidewire. In particular, the guidewire lumen extends into (and through at least a part of) the tip section.

In certain embodiments, the positional identifier/marker of the present invention includes at least one element (e.g. a first element), wherein the (first) element is arranged such that a rotational orientation and/or an axial orientation and/or a tilted orientation of the tip section relative to the surrounding tissue is discernable, particularly during deployment of the heart valve implant.

In certain embodiments, the positional identifier/marker includes at least one further element.

In certain embodiments, the positional identifier/marker of the present invention includes at least two elements (e.g. a first element and a second element), wherein the elements (e.g. the first and second elements) are arranged with respect to each other such that a rotational orientation and/or an axial orientation and/or a tilted orientation of the tip section relative to the surrounding tissue is discernable, particularly during deployment of the heart valve implant.

With the above context, according to the present invention the the element(s) of the positional identifier/marker may assume any geometric shape that allows for a clear positional identification of a medical implant in terms of a rotational orientation and/or an axial orientation and/or a tilted orientation; e.g. under fluoroscopy conditions from an outside of a human or animal body.

With the context of the present invention, a geometric shape may be, e.g., a dot, a line, a triangle, a square, a pentagon etc., a graphical sign, a number, e.g. an Arabic number, a letter, e.g. a Latin letter, an arrow, an arrowhead, an open circle, a wave, an angle, but not limited to, and any kind of combinations thereof.

Following the above, in certain embodiments, the positional identifier/marker of the present invention includes a first element and a second element, wherein the first element and the second element are arranged with respect to each other such that a rotational orientation and/or an axial orientation and/or a tilted orientation of the tip section relative to the surrounding tissue is discernable, particularly during deployment of the heart valve implant.

A positional identifier/marker having more than one positional identifier element/marker element advantageously allows to determine the correct rotational position of the catheter (and thus the heart valve implant), e.g., when viewed from different angles.

In certain embodiments, the first element extends in an axial direction in respect of the longitudinal axis (i.e., parallel to the longitudinal axis) and the second element extends in a radial or circumferential direction in respect of the longitudinal axis (i.e., perpendicular to the longitudinal axis).

This configuration ensures that at least one of the elements is visible well when the tip section is observed from different angles. For instance, the element extending in the axial direction is visible well when viewed from the side of the tip section and the element extending in the radial or circumferential direction is visible well when viewed from the tip of the tip section and/or from the side of the tip.

In certain embodiments, the positional identifier/marker further includes a third element, wherein particularly the third element is perpendicular to the first element and/or the second element. A third element further improves visibility of the positional identifier/marker from different angles.

Thus, in certain embodiments of the invention the positional identifier/marker includes at least three elements.

In certain embodiments, the first element appears, e.g., as a dot and the second element appears, e.g., as a line when viewed from the tip of the tip section in the direction of the longitudinal axis or in a plane arranged perpendicular to the longitudinal axis.

Due to the appearance of the elements as a dot and a line, the first and the second element can be clearly distinguished, allowing the physician to discern the correct rotational orientation of the tip section and thereby the stent portion of the heart valve implant. In certain embodiments, the positional identifier/marker, the first element, the second element and/or the third element is shaped such that they are forming a letter, preferably a Latin letter of Latin script.

In certain embodiments, the positional identifier/marker, the first element, the second element and/or the third element is shaped such that they are forming the letter B, the letter H, the letter L, the letter T or the letter V or shaped as an arrow, particularly when viewed in a direction perpendicular to the longitudinal axis or in a plane parallel to the longitudinal axis.

In certain embodiments, the first element forms a notch, wherein the second element is arrangeable in the notch (e.g. such as a bead), particularly when viewed from the tip of the tip section in the direction of the longitudinal axis or in a plane arranged perpendicular to the longitudinal axis, such that a rotational orientation of the tip section relative to the surrounding tissue is discernable, particularly during deployment of the heart valve implant. This arrangement of the first element and the second element can also be described as a notch and bead configuration (in the sense of notch and bead sights).

While using such a notch and bead configuration for a positional identifier/marker in accordance with the invention, in addition to identifying the correct rotational orientation and/or axial orientation and/or tilted orientation of the tip section, the physician is able to determine the correct viewing angle onto the tip section (e.g. a view in a plane perpendicular to the longitudinal axis), because the bead will appear to be placed within the notch only when viewed in the correct plane.

In certain embodiments, the first element is positioned on a first side radially outside of the longitudinal axis, e.g. of the tip section, and the second element is positioned on a second side radially outside of the longitudinal axis opposite the first side, e.g. of the tip section. In certain embodiments, the first element is positioned on a first side radially outside of the longitudinal axis, e.g. of the tip section, the second element is positioned on a second side radially outside of the longitudinal axis, e.g. of the tip section, and the third side is positioned on a third side radially outside of the longitudinal axis, e.g. of the tip section.

In certain embodiments, the tip section includes or consists of a radiotransparent material, wherein the positional identifier/marker includes or consists of a radiopaque material. This results in good visibility of the positional identifier/marker without obstruction by the remaining tip section. In addition, embedding the positional identifier/marker within the material of the tip section, which ensures a smooth atraumatic surface of the tip section, does not interfere with visibility.

In the context of the present specification, the term “radiopaque” means obstructing (i.e., not allowing) the passage of radiant energy, particularly X-rays. The term “radiotransparent” in the context of the present specification means transparent to radiation, particularly X-rays, i.e., invisible or essentially invisible, under X-ray illumination or fluoroscopy.

In certain embodiments, the tip section includes or consists of a radiopaque material, wherein the marker includes or consists of a radiotransparent material.

In certain embodiments, the positional identifier/marker is formed by a recess in the radiopaque material of the tip section.

In certain embodiments, the tip section includes a radiopaque material, wherein the positional identifier/marker includes the radiopaque material at a different concentration from the remaining tip section, resulting in a radiographic contrast between the tip section and the positional identifier/marker.

In certain embodiments, the tip section includes a first radiopaque material such as a polymer including $BaSO_4$ (barium sulphate), whereas the positional identifier/marker itself includes a second radiopaque material different from the first radiopaque material such as gold, platinum, iridium, tantalum, tungsten and the like, resulting in a radiographic contrast between the tip section and the positional identifier/marker.

By using negative contrast in the way described above, i.e., where the positional identifier/marker results in lower contrast under X-ray illumination than the remaining tip section, visibility of the positional identifier/marker is ensured also in cases where the radiopacity of the tip section as a whole is required.

In certain embodiments, the radiopaque material is selected from a group consisting of barium sulphate ($BaSO_4$), tungsten, tantalum, bromine, iodine, iodide, titanium oxide, platinum, gold, zirconium oxide, bismuth and combinations thereof. In general, with the context of the present invention, any material is suitable as radiopaque material that allows for a sufficient contrast, but simultaneously is biocompatible.

In certain embodiments, the tip section includes or consists of a first radiopaque material, particularly barium sulphate ($BaSO_4$), wherein the marker consists of a second radiopaque material different from the first radiopaque material, and wherein the second radiopaque material exhibits a radiographic contrast to the first radiopaque material, such as tungsten, tantalum, bromine, iodine, iodide, titanium oxide, platinum, gold, zirconium oxide, bismuth and combinations thereof.

In certain embodiments, the positional identifier/marker is arranged on the surface of the tip section.

In an embodiment, the positional identifier/marker is made from a radiopaque material and may be glued on the catheter tip. Optionally, the catheter tip has a corresponding recess for receiving the positional identifier/marker and so to avoid any protruding edges and for the sake of strengthening the attachment.

In an embodiment, the positional identifier/marker as such as a structure or the like may be painted/sprayed on the catheter tip using a stencil, if necessary. Thereby, e.g., marker-containing color/lacquer may be used.

In an embodiment, the positional identifier/marker may be applied as a radiopaque material in the surface area of the catheter tip while using a suitable sputtering process (e.g. sputter deposition/sputter coating). If indicated, some sort of a template on the surface of the catheter tip may be used in order to achieve the desired positional identifier/marker shape.

In an embodiment, the positional identifier/marker is embedded in the catheter tip by a suitable embedding technique.

In an embodiment, the catheter tip itself is a readily 3D-printed part already including a positional identifier/marker in accordance with the present invention.

As mentioned above, a catheter tip with a radiopaque material as positional identifier/marker may be manufactured by a suitable 3D-printing technique. Thereby, locally a radiopaque material is incorporated during a 3D-printing process in a catheter tip made from a polymer. For instance, locally $BaSO_4$ may be admixed to the polymer of the catheter tip 3D-printing process in order to result in a local radiopaque positional identifier/marker.

In view of the above, a tip section with a positional identifier/marker thereon can be easily manufactured, and the desired positional identifier/marker arrangement can be varied according to the needs of the particular application.

As mentioned above, in certain embodiments, the positional identifier/marker is embedded within the tip section.

In other words, the positional identifier/marker is positioned below the surface of the tip section with the material of the remaining tip section surrounding the positional identifier/marker. This can be achieved by introducing the positional identifier/marker during manufacturing of the tip section. For example, the tip section may be extruded or molded from a plastic material, and the positional identifier/marker material may be integrated into the tip section during extrusion or molding. In particular, if the remaining tip section includes or is formed from a radiotransparent material, the embedded positional identifier/marker can be visualized, e.g., by fluoroscopy even though the material or the tip section is disposed around it.

Embedding the positional identifier/marker within the tip section prevents the positional identifier/marker from protruding from the tip section, resulting in better atraumatic properties of the tip section, which is important, e.g., during steering of the catheter through narrow and curved blood vessels without causing damage to the vessel walls.

In certain embodiments, the catheter includes a connector for fixing the frame structure such as a stent portion of the heart valve implant to the catheter, particularly to the inner shaft, particularly in a rotationally fixed arrangement in respect of a rotation around the longitudinal axis.

Such connectors provide a reliable connection of the stent portion to the catheter, which is especially important when the heart valve implant is partially deployed and then recaptured to reposition the stent. When the stent portion is in its desired final position, the connection between the connector and the stent portion can be released.

In certain embodiments, the connector is rotationally fixed to the inner shaft with respect to a rotation around the longitudinal axis.

Thereby, the stent portion is kept in a defined rotational orientation relative to the marker on the tip section, which is also rotationally fixed to the inner shaft, such that the positional identifier/marker indicates the current rotational orientation of the stent portion.

In certain embodiments, the connector includes at least one recess, wherein the recess is configured to receive a connecting element of the frame structure such as a stent portion of the heart valve implant to fix the stent portion to the catheter, particularly in the radially compressed state.

In certain embodiments, the connector includes a plurality of recesses, wherein the recesses are configured to receive respective connecting elements of the frame structure such as a stent portion of the heart valve implant to fix the stent portion to the catheter, particularly in the radially compressed state.

In certain embodiments, the connector includes at least one protrusion, wherein the protrusion is configured to receive a connecting element of the frame structure such as a stent portion of the heart valve implant to fix the stent portion to the catheter, particularly in the radially compressed state.

In certain embodiments, the connector includes a plurality of protrusions, wherein the protrusions are configured to receive respective connecting elements of the frame structure such as a stent portion of the heart valve implant to fix the stent portion to the catheter, particularly in the radially compressed state.

A second aspect of the invention relates to an assembly including a catheter according to the first aspect of the invention and a heart valve implant including a frame structure such as a stent portion. The stent portion is received by the inner shaft of the catheter, particularly in a radially compressed state. In particular, the heart valve implant further includes a plurality of valve leaflets attached to the stent portion.

Wherever alternatives for single separable features are laid out herein as "embodiments", it is to be understood that such alternatives may be combined freely to form discrete embodiments of the invention disclosed herein.

FIG. 1 shows a longitudinal sectional view of a distal part of a catheter 100 according to the present invention for deployment of a heart valve implant 200 in a human or animal body.

Figure 3A:
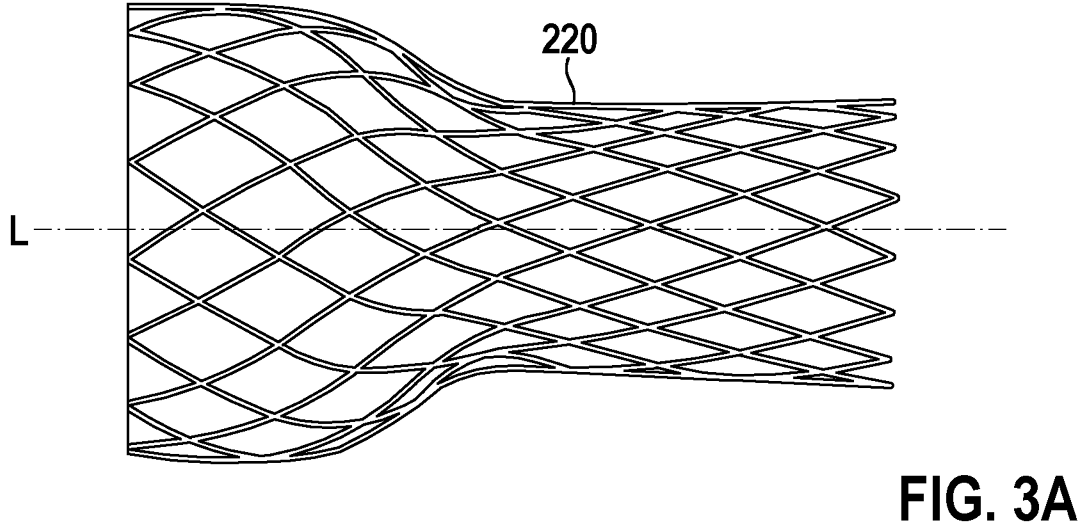
FIGS. 3A-3C schematically show a heart valve implant of the assembly according to the present invention.
Figure 3B:
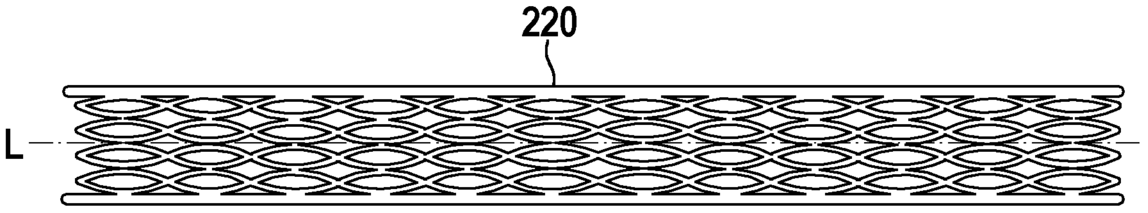
Figure 3C:
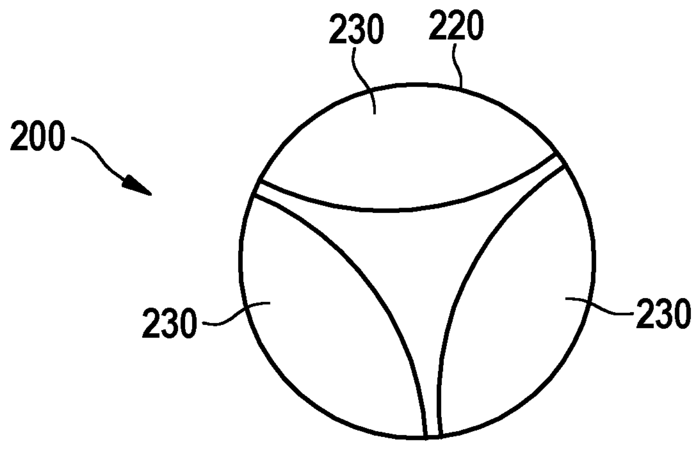

A schematic view of the heart valve implant 200 is shown in FIG. 3, wherein FIG. 3A shows a side view of the radially expanded configuration of the stent portion 210, FIG. 3B shows a side view of the radially compressed configuration of the stent portion 210, and FIG. 3C shows a top view of the heart valve implant 200 showing the valve leaflets 230 (particularly from bovine or porcine pericardium or a synthetic material) replacing the function of the native heart valve leaflets of, e.g., the aortic valve, arranged in and connected to the stent portion 210, particularly in the radially expanded state.

The catheter 100 extends along a longitudinal axis L between a proximal end (not shown) and a distal end D. The proximal end is oriented towards the physician operating the catheter 100 and the distal end D is oriented towards the heart of the patient during deployment of the heart valve implant 200.

The catheter 100 includes an inner shaft 110 and an outer shaft 120 arranged concentrically around the inner shaft 110, both extending along the longitudinal axis L. The inner shaft 110 forms a first guidewire lumen 111 for receiving a guidewire configured to steer and stabilize the catheter 100 during navigation through the blood vessels of the patient.

At its distal end, the inner shaft 110 is connected to a conical tip section or nosecone 130. The tip section 130 includes a tip 131 that forms the distal end D of the catheter 100 and particularly includes a second guidewire lumen 132 for receiving the guidewire, wherein the second guidewire lumen 132 is particularly continuous with the first guidewire lumen 111 of the inner shaft 110. The tip section 130 is particularly formed from a smooth atraumatic material. By means of the conical tip section 130 at the distal end D, the catheter 100 may be navigated through bends and obstructions in the patient blood vessels to access the heart.

In view of the above, the skilled person readily understands that the specified first and second guidewire lumen build up one coherent guidewire lumen for passage of the guidewire. But with the context of the present invention for mere formal reasons it is at certain instances referred to as a first guidewire lumen of the overall catheter part discriminating from the second guidewire lumen of the distal tip part, e.g. of a nosecone.

The inner shaft 110 is further configured to receive a stent portion 210 of a heart valve implant 200 (as shown in FIGS. 3A-C) in its radially compressed configuration, wherein particularly the stent portion 210 is crimped on the inner shaft 110. As shown in FIG. 1, the distal part of the inner shaft 110 is surrounded by a capsule 121 (particularly from a metallic material), wherein the stent portion 210 of the heart valve implant 200 is arranged between the inner shaft 110 and the capsule 121 and the capsule 121 shields the stent portion 210 from the outside environment in the crimped state. The capsule 121 is connected to the distal end of the outer shaft 120, which has a slightly smaller diameter than the capsule 121, by a tapered connection 122. The capsule 121 (and particularly also the outer shaft 120 of the catheter)

is retractable relative to the inner shaft 110 in the proximal direction to deploy the heart valve implant 200 at its target site in the native valve annulus (particularly of the aortic valve). This retracting motion can be particularly controlled by the physician at a handle at the proximal end of the catheter 100 (not shown). The capsule 121 may also be movable in the distal direction in respect of the inner shaft 110 to recapture the stent portion 210.

Of course, the scope of the invention also includes catheters 100 without a capsule 121; e.g. in case of a balloon-expandable catheter.

In another case, the stent portion 210 may be disposed between the inner shaft 110 and the outer shaft 120, and the heart valve implant 200 may be deployed by retracting the outer shaft 120 in the proximal direction relative to the inner shaft 110, and optionally recaptured by moving the outer shaft 120 in the distal direction relative to the inner shaft 110.

Figure 2:
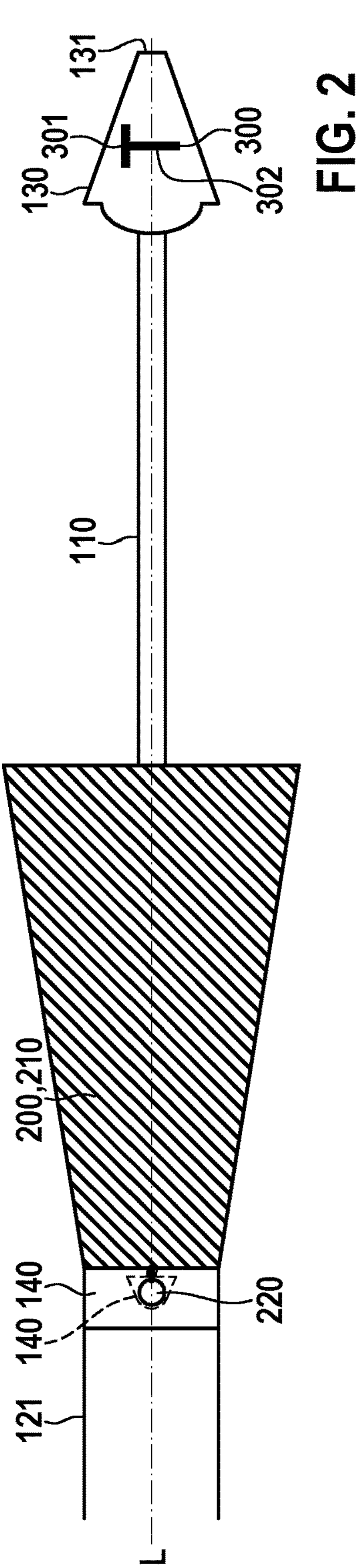
FIG. 2 shows a schematic side view of an exemplary catheter according to the present invention with a retracted capsule and a partially deployed schematic heart valve implant.

FIG. 2 shows a side view of the same embodiment of the catheter 100 as shown in FIG. 1, with the capsule 121 being retracted and the heart valve implant 200 being partially deployed. As best observed in FIG. 2, the stent portion 210 of the heart valve implant 200 is fixed to the catheter 100 by a connector 140 which is connected and rotationally fixed to the inner shaft 110. Herein, exemplarily, the connector 140 includes a plurality of recesses 141 around the circumference of the connector 140 in respect of the longitudinal axis L (one exemplary recess 141 is shown in FIG. 2), and the stent portion 210 of the heart valve implant 200 includes a plurality of corresponding connecting elements 220 configured to engage into respective recesses 141 of the connector 140, so to fix the stent portion 210 to the connector 140. Typically, in case of a self-expanding stent the prosthesis expands itself without the aid of a separate mechanism for a controlled release. In one embodiment, however, the catheter 100 may further include an additional or a sole release mechanism (particularly an actuatable one at the proximal handle) configured to move the connecting elements 220 out of the recesses 141 and so to release the heart valve implant 200 from the catheter 100.

According to the invention, the stent portion 210 of the heart valve implant 200 is rotationally fixed to the inner shaft 110 meaning that the stent portion 210 and the inner shaft 110 cannot be rotated around the longitudinal axis L relative to each other. This may be achieved by the connector 140, particularly by the recesses 141 of the connector 140 receiving the connecting elements 220 of the stent portion 200. Likewise, the tip section 130 is rotationally fixed to the inner shaft 110, such that the tip section 130 cannot be rotated relative to the inner shaft 110 around the longitudinal axis L. This results in a fixed rotational arrangement between the tip section 130 and the stent portion 210 of the heart valve implant 200 mounted on the catheter 100.

As shown in FIGS. 1 and 2 and depicted in detail in FIGS. 4A-H as well as in FIGS. 5A-D, the tip section 130 includes a positional identifier/marker 300 to indicate the rotational orientation and/or axial orientation and/or tilted orientation of the catheter 100, particularly of the stent portion 210 of the heart valve implant 200 mounted to the catheter 100. The positional identifier/marker 300 can be viewed from outside of the human or animal body when the catheter 100 is disposed in the patient blood vessels and/or heart during the catheterization procedure. This may be achieved for instance through a positional identifier/marker 300 made from or including a radiopaque material which can be viewed from outside the body using, e.g., fluoroscopy. Alternatively, the positional identifier/marker 300 may be formed from a radiotransparent material, whereas the remaining tip section 130 is made from a radiopaque material, or the positional identifier/marker 300 may be formed by at least one recess in a radiopaque material. The positional identifier/marker 300 may be arranged on the surface of the tip section 130 or may be embedded within the tip section 130.

In an embodiment, the positional identifier/marker or rotational/axial/tilted alignment may also be additionally realized/imaged on the outside of the catheter tip and/or handle (e.g. via an imprint with a color), so that a physician is allowed to recognize how the catheter is assembled before it is inserted and without the use of an X-ray device. This allows the physician to insert the catheter in a desired pre-alignment form.

FIGS. 4A-H show different shapes of positional identifiers/markers 300 on tip sections 130 of a catheter 100 according to the invention; especially different geometric shapes in accordance with the invention. In each case, the right panels of FIGS. 4A-H show respective top views along the longitudinal axis L and the left panels of FIGS. 4A-H are respective side views along the longitudinal axis L starting from the tip 131 of the respective tip section 130 (like in FIG. 1 but in perpendicular orientation and not in horizontal orientation).

Figure 4A:
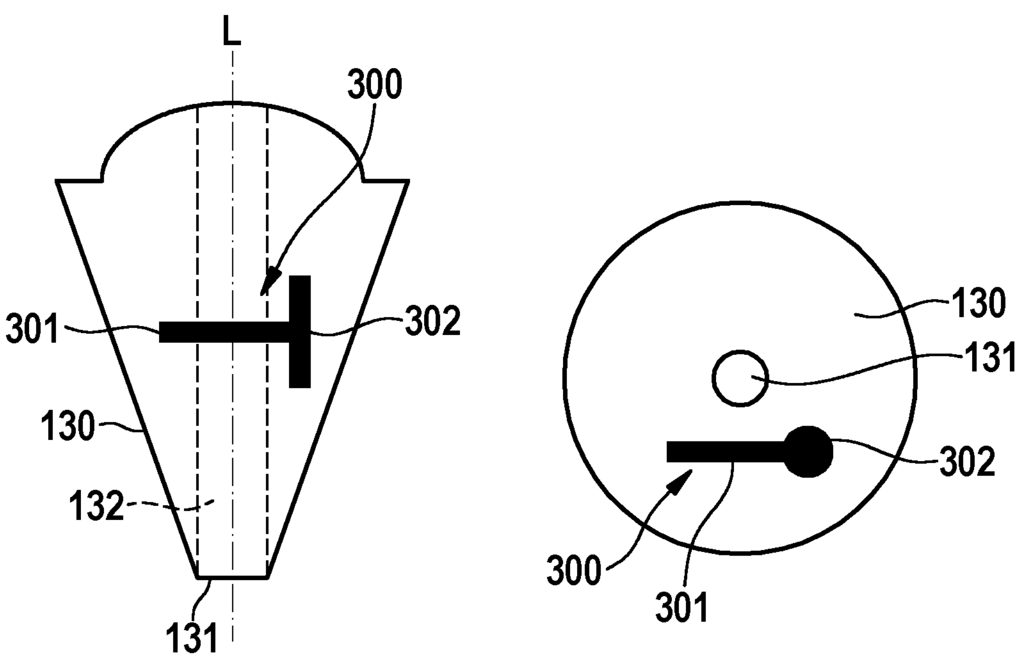
FIGS. 4A-4H show exemplary tip sections of the catheter according to the invention carrying different embodiments of positional identifiers/markers.

FIG. 4A illustrates a positional identifier/marker 300 resembling the letter T in a side view (FIG. 4A left), wherein a first element 301 (the first arm of the T) extends along a circumferential direction in respect of the longitudinal axis L and appears as a line in the front view of FIG. 4A right, and a second element 302 of the positional identifier/marker 300 (the second arm of the T) extends along an axial direction in respect of the longitudinal axis L and appears as a dot adjacent to the line formed by the first element 301 in the front view of FIG. 4A right.

Figure 4B:
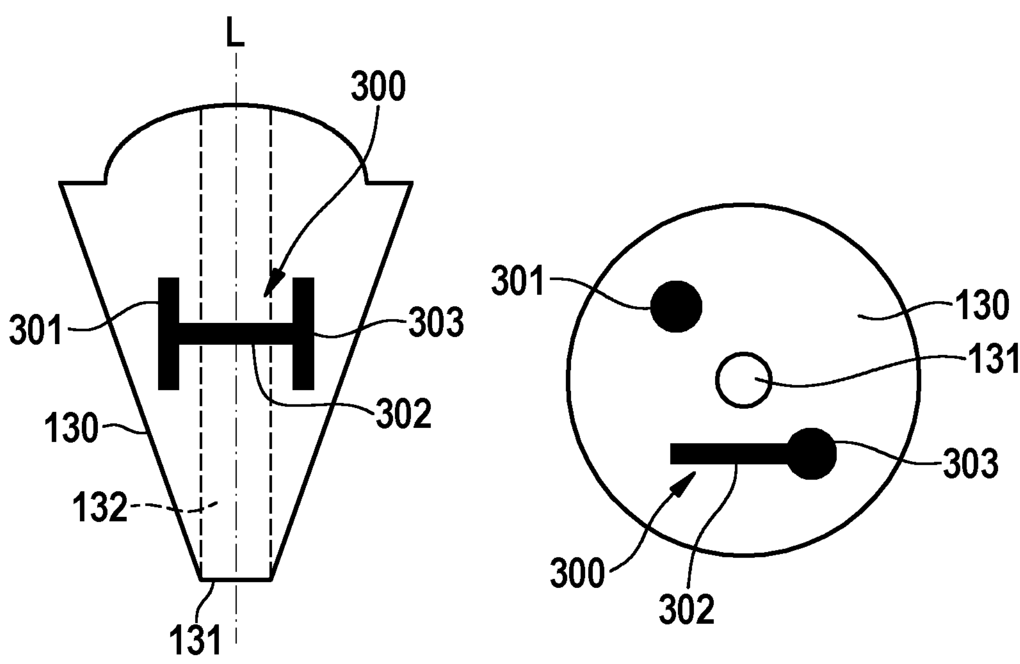

A similar arrangement of a positional identifier/marker 300, but with a first element 301, a second element 302 and a third element 303 is shown in FIG. 4B. The elements 301, 302, 303 together resemble the letter H in the side view of FIG. 4B left. In the front view shown in FIG. 4B right, the first element 301 appears as a dot positioned on a first side of the tip 131, the second element 302 appears as a line, and the third element 303 appears as a dot adjacent to the line formed by the second element 302 and arranged on a second side of the tip 131, opposite the first side. For example, these dots formed by the first and second element 301, 302 may indicate the positions of the coronary ostia in the desired rotational/axial/tilted position of the stent portion 210.

Figure 4C:
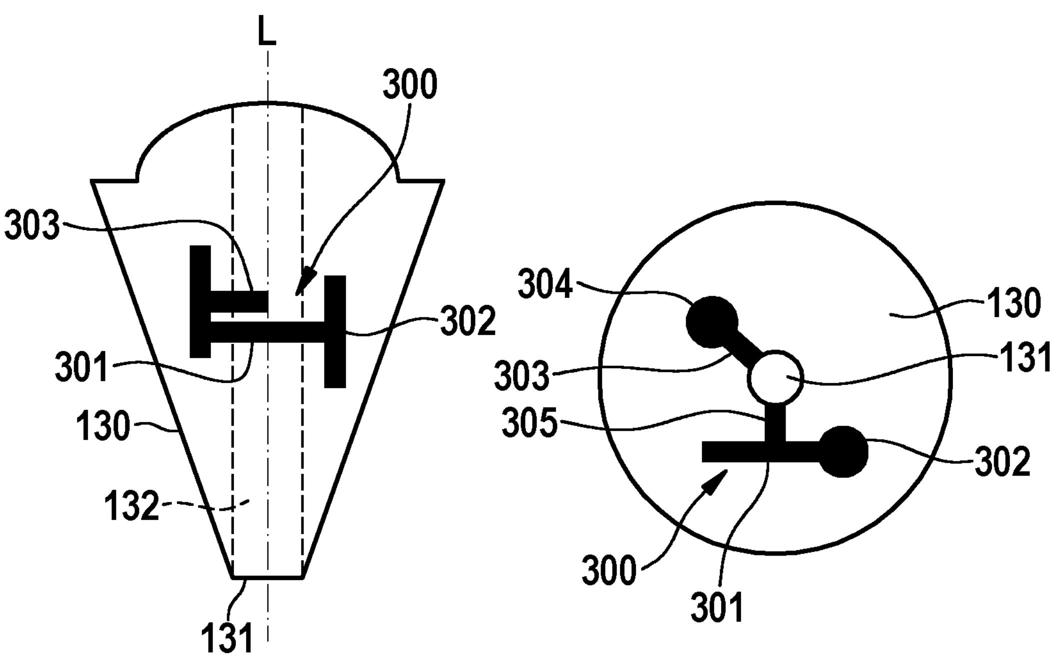

FIG. 4C shows a positional identifier/marker including a first element 301, a second element 302 and a third element 303, together forming a letter T in the side view of FIG. 4C left similar to the positional identifier/marker 300 shown in FIG. 4A with an additional line parallel to one arm of the T formed by the third element 303. In the front view of FIG. 4C right, a shape similar to that depicted in FIG. 4B right is formed, including two dots on opposite sides of the tip 131 formed by the second element 302 and a fourth element 304 not visible in the side view of FIG. 4C left, a line formed by the first element 301, and two additional lines formed by the third element 303 and a fifth element 305 not visible in FIG. 4C left. The two additional lines formed by the third and fifth element 303, 305 connect the tip 131 with the line formed by the first element 301 and the dot formed by the fourth element 304, respectively.

Figure 4D:
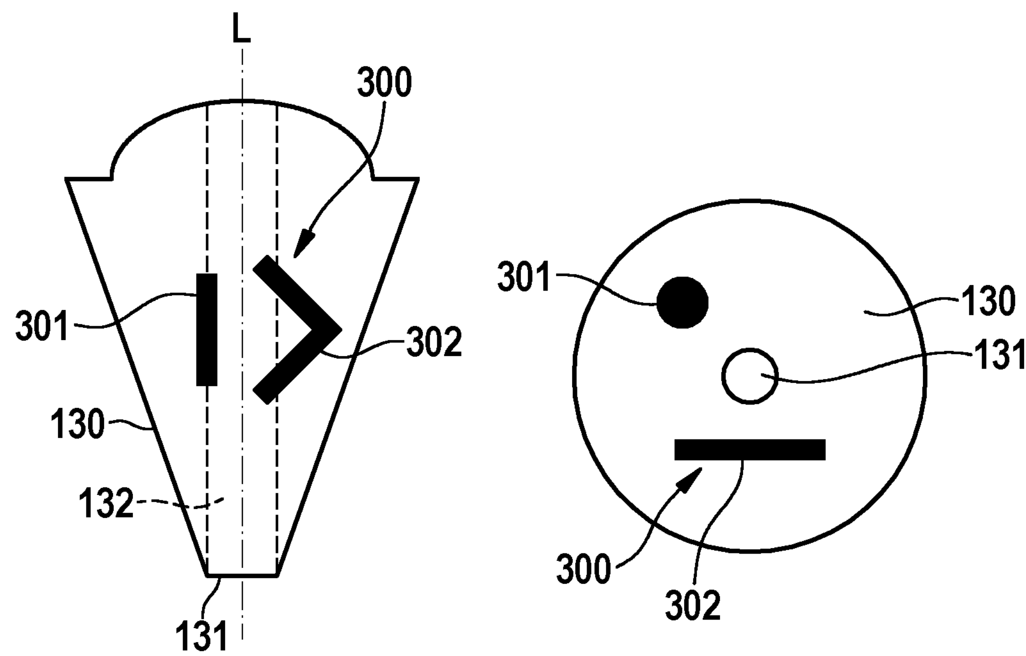

FIG. 4D depicts a further positional identifier/marker 300 which in the side view of FIG. 4D left is composed of a line formed by a first element 301 extending in the axial direction and a V-shaped or arrow-shaped second element 302 adjacent the first element 301, with the tip of the V pointing away from the first element 301 in the circumferential direction. In the front view of FIG. 4D right, the first element 301 forms a dot on a first side of the tip 131 and the second element 302 forms a line on a second side of the tip 131 opposite the first side.

Figure 4E:
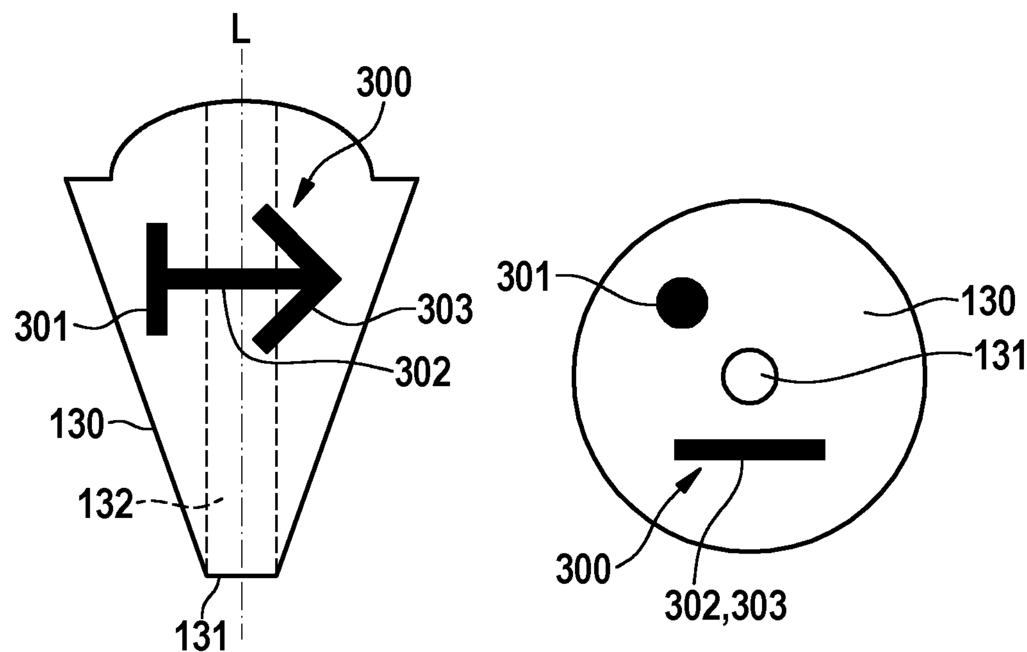

The embodiment of the positional identifier/marker 300 shown in FIG. 4E appears as an arrow-like shape in the side view of FIG. 4E left including a first element 301 appearing as an axial line, a second element 302 appearing as a circumferential line extending between the first element 301 and a V-shaped third element 303 with the tip of the V pointing in the circumferential direction away from the first element 301. In the front view of FIG. 4E right, this results in a dot on a first side of the tip 131 formed by the first element 301 and a line on a second side of the tip 131 opposite the first side, formed by the overlapping second and third elements 302, 303.

Figure 4F:
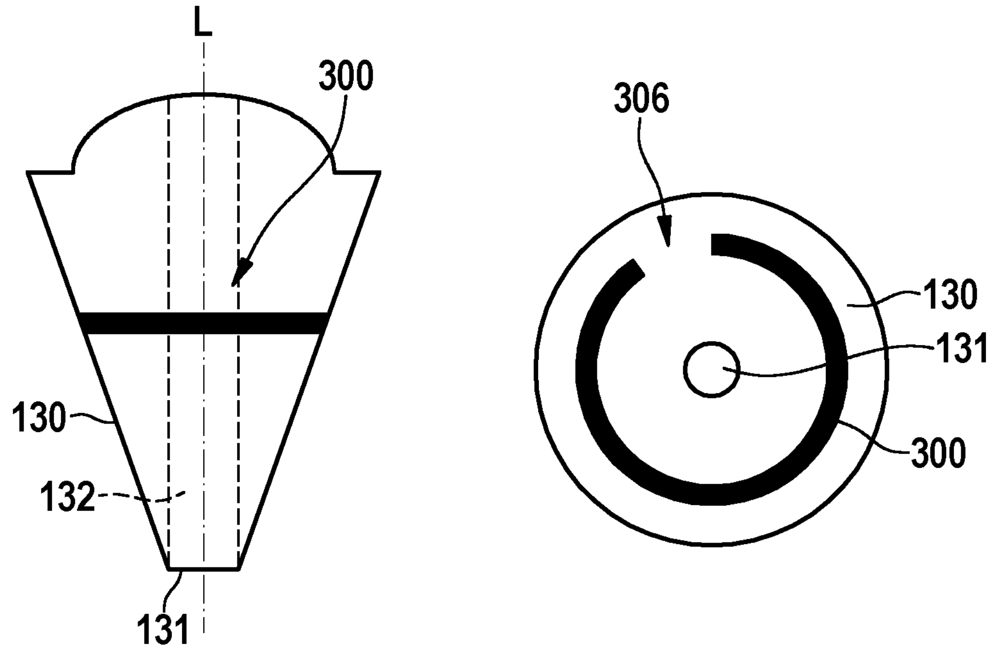

FIG. 4F shows a positional identifier/marker 300 shaped as a broken ring or open circle, respectively, around the circumference of the tip section 130. The marker appears as a circumferential/radial line in the side view of FIG. 4F left and as a broken circle or open circle having a gap 306 in the front view of FIG. 4F right. Here, the gap 306 may indicate the position of a coronary ostium in the desired rotational position of the heart valve implant 200.

Figure 4G:
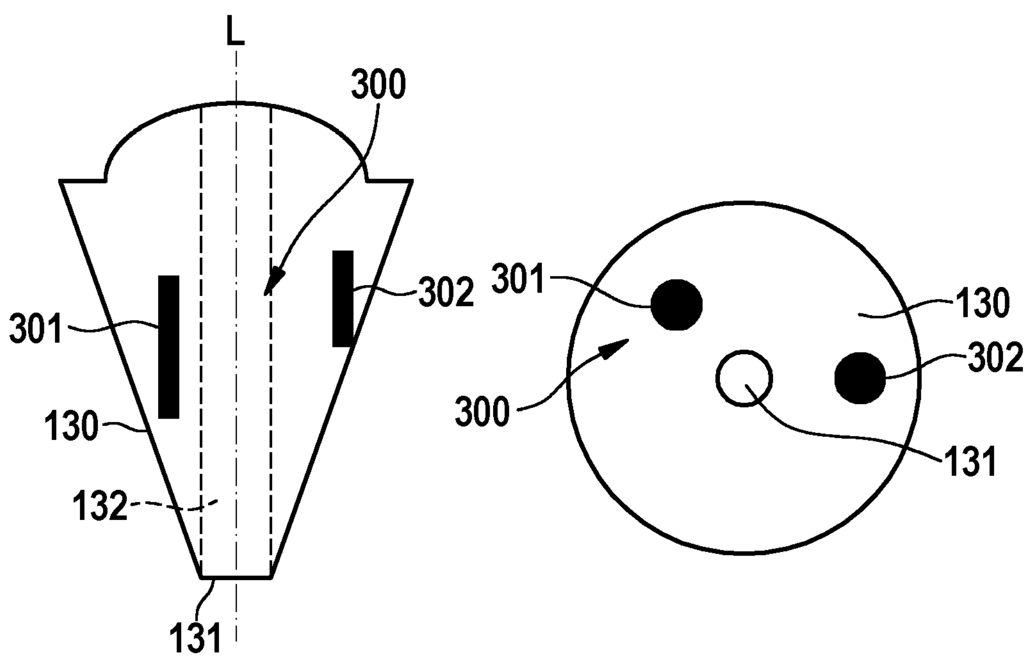

A further embodiment of the positional identifier/marker 300 is shown in FIG. 4G. This positional identifier/marker 300 includes a first element 301 and a second element 302 appearing as parallel axial lines of different length in the side view of FIG. 4G left and as dots in the front view of FIG. 4G right, wherein the dots may indicate the position of coronary ostia in the desired position. In an embodiment, these lines may have the same length, but with the proviso that both lines are not arranged with a 180° symmetry; this will result in X-ray in some sort of a parallel line to the guidewire, thereby indicating a rotational orientation.

Figure 4H:
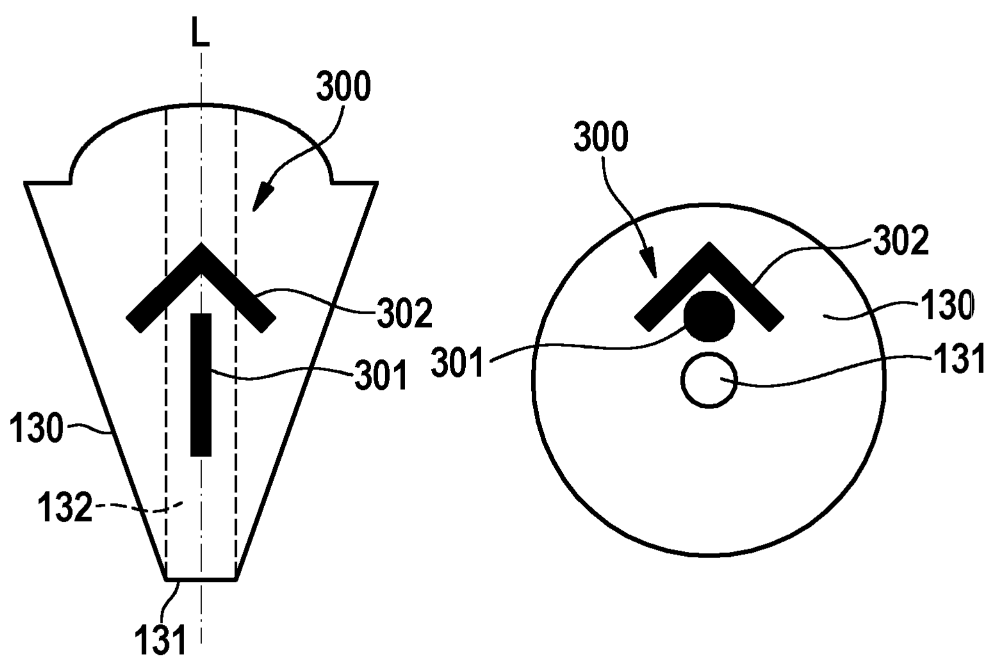
Figure 5A:
FIGS. 5A-5D show further exemplary tip sections of the catheter according to the invention carrying different embodiments of positional identifiers/markers.
Figure 5A:
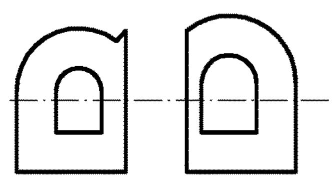
Figure 5A:
Figure 5A:
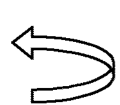
Figure 5A:
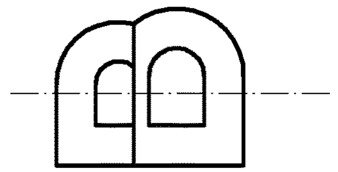
Figure 5A:
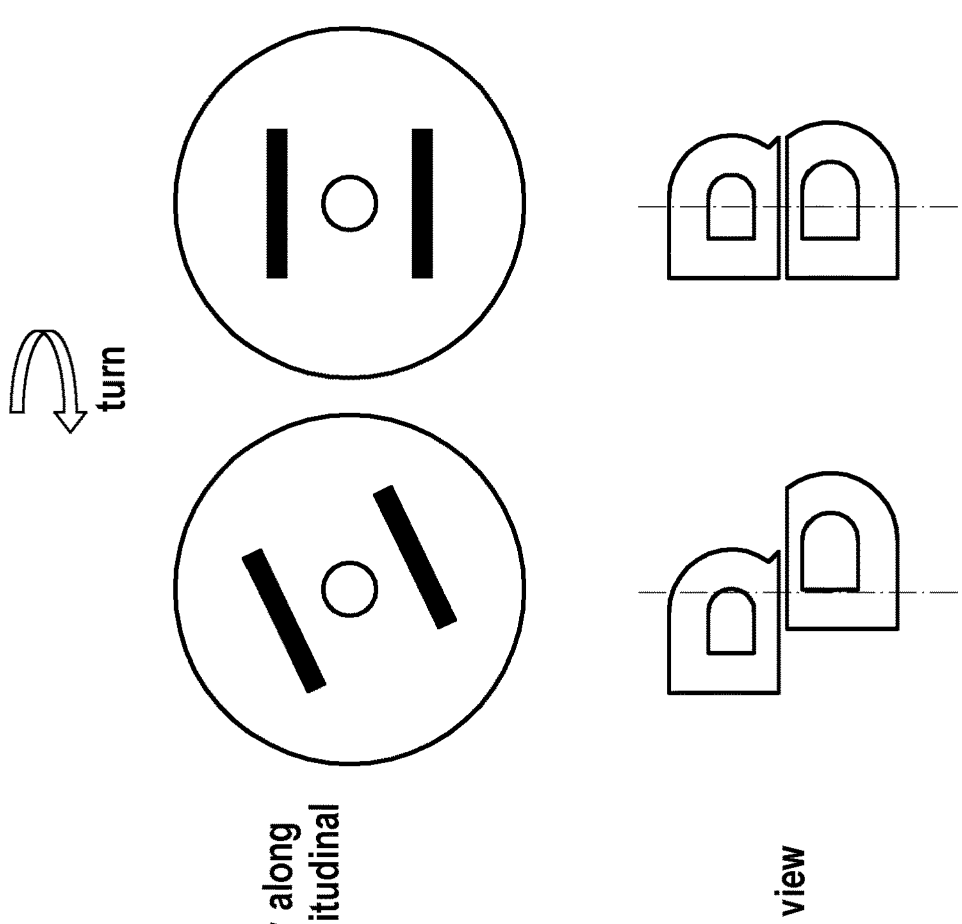
Figure 5B:
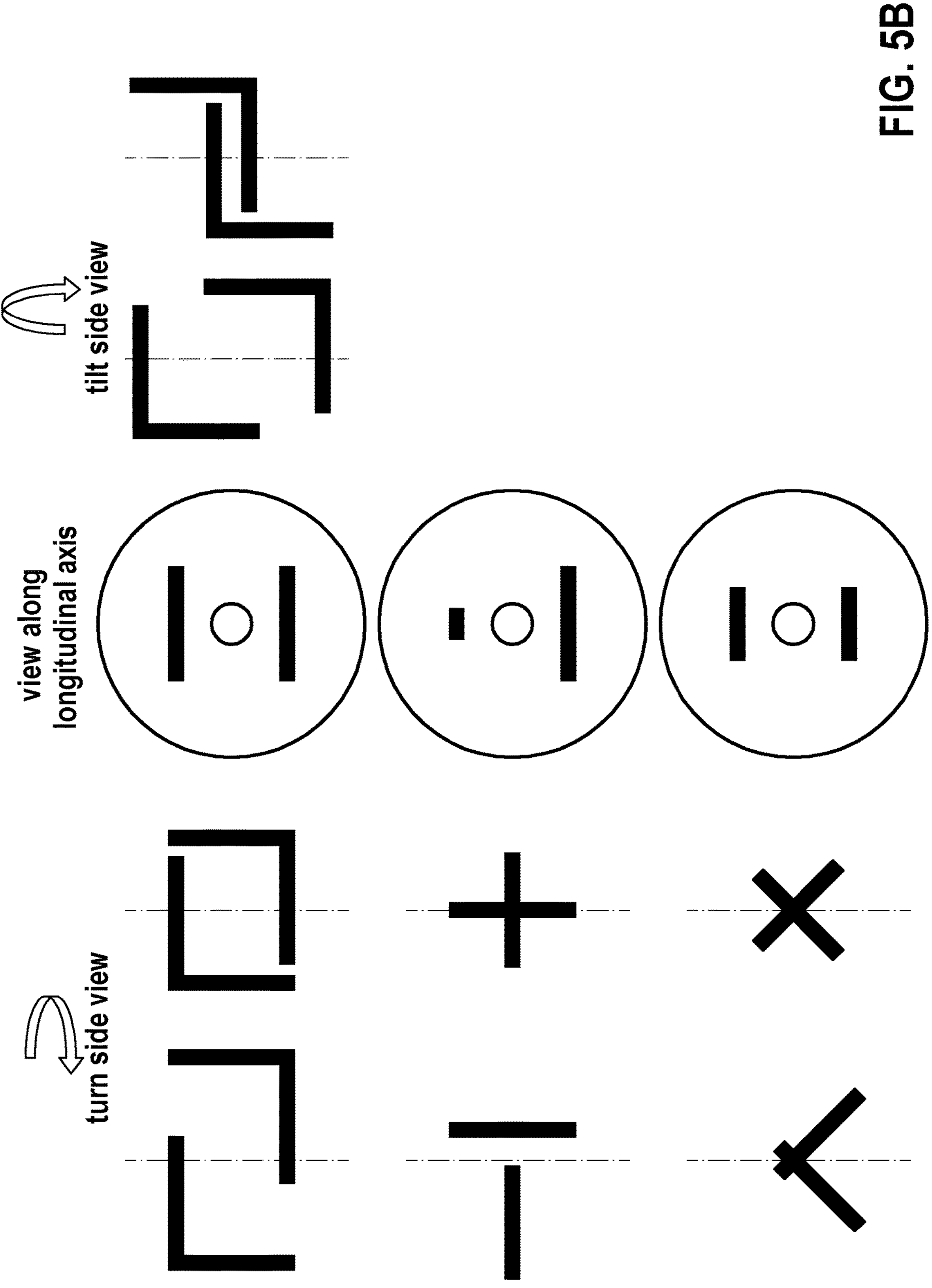
Figure 5C:
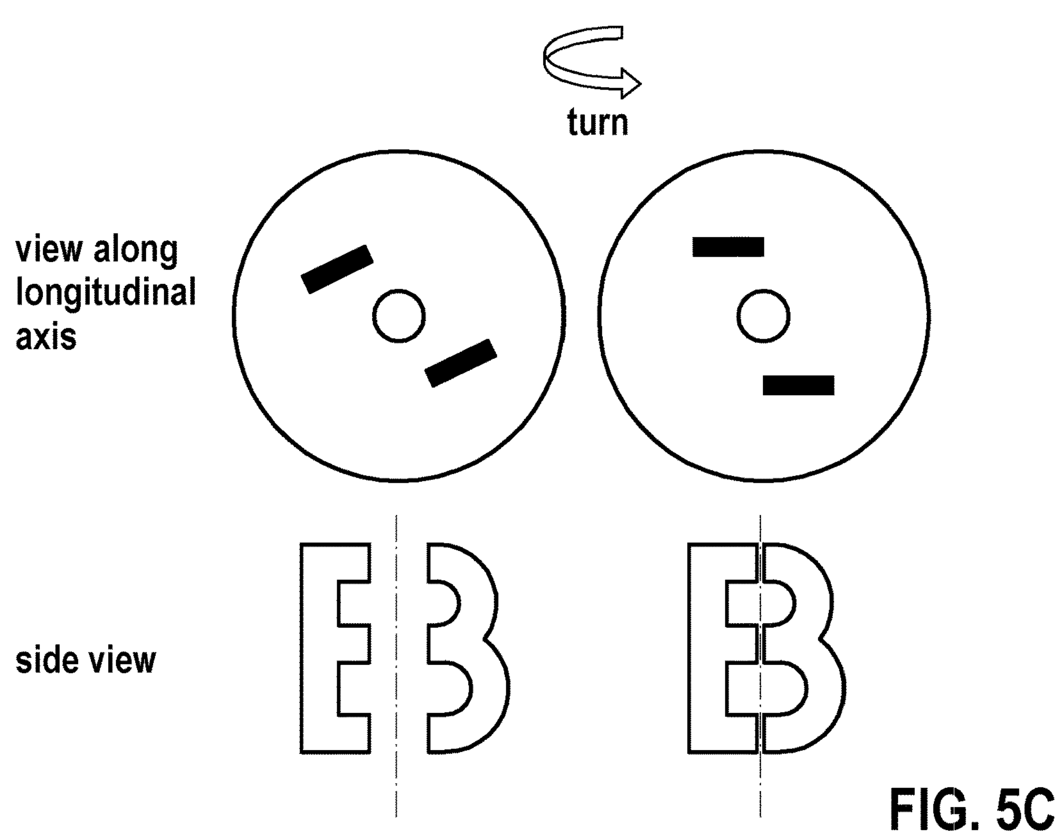
Figure 5D:
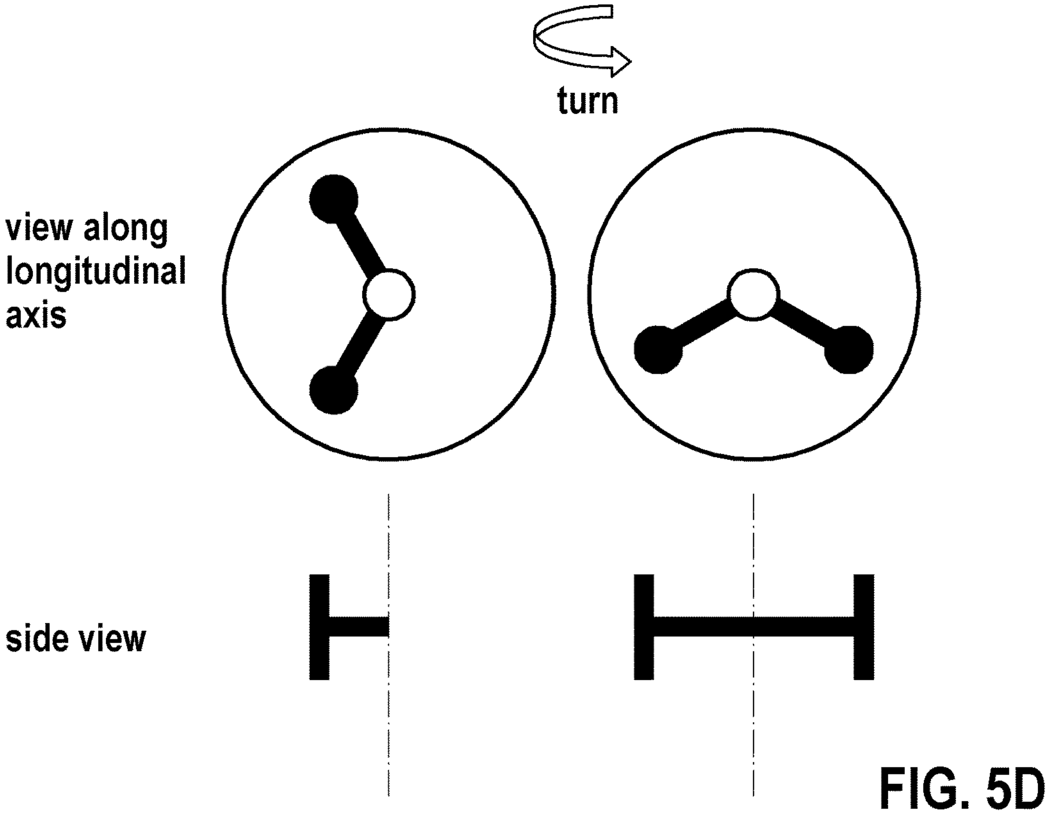

Finally, FIG. 4H depicts a positional identifier/marker 300 forming a notch-and-bead configuration. In the side view of FIG. 4H left, a first element 301 of the positional identifier/marker 300 appears as an axial line, and a second element 302 of the positional identifier/marker 300 appears as a V-shape with the pointed end of the V pointing away from the first element 301 in the axial direction. This results in a notch-and-bead pattern in the desired viewing angle (a plane perpendicular to the longitudinal axis L), as shown in FIG. 4H right. There, the first element 301 appears as a dot or bead, and the second element 302 appears as a V-shape forming a notch. To obtain the correct viewing plane, the bead has to be placed above the notch formed by the V-shape. Subsequently, the point of the V-shape may be used as a rotational indicator, e.g., pointing towards a coronary ostium in the desired position.

In line with the principles described above for FIGS. 4A-H, the FIGS. 5A-D show further different shapes of positional identifiers/markers 300 on tip sections 130 of a catheter 100 according to the invention, and thus indicating a rotational and/or axial and/or tilted orientation of the catheter, especially the catheter tip, and a medical implant affixed to the catheter.

In an exemplary deployment procedure of the heart valve implant 200 using the catheter 100 according to the invention, the physician inserts the catheter 100 with a heart valve implant 200 crimped on the inner shaft 110 and positioned between the inner shaft 110 and the outer shaft 120 or capsule 121 into an artery of the patient (e.g. the femoral artery) with the tip 131 of the tip section 130 ahead. The catheter 100 is then advanced towards the aortic valve via the patient arterial system, optionally steered by a mechanism at the handle at the proximal end of the catheter 100 controlling a pull wire. Under fluoroscopic imaging the positioning of the catheter 100 in the patient body can be followed by the physician.

When the catheter 100 has reached its desired position, with the heart valve implant 200 in the native aortic valve and the tip section 130 particularly reaching into the left ventricle, the rotational orientation and/or axial orientation and/or tilted orientation of the catheter 100 is controlled by visualizing the positional identifier/marker 300 on the tip section 130 by fluoroscopy and the rotational orientation may be adjusted using the handle until the desired orientation is reached, particularly such that the struts of the stent portion 210 do not obstruct the coronary ostia.

When the stent portion 210 is in the desired orientation axially and rotationally, and in terms of a tilted orientation, the outer shaft 120 or capsule 121 is retracted relative to the inner shaft 110, thereby exposing the stent portion 210 of the heart valve implant 200. The stent portion 210 is then radially expanded at least partially either due to its self-expanding properties or by a force-expandable mechanism such as a balloon where no capsule is needed. At this time, the connector 140 particularly still holds one end of the stent portion 210 on the inner shaft 110, such that the stent portion 210 may be recaptured in the capsule 121 or outer shaft 120 if the placement of the stent portion 210 needs to be corrected. During such a repositioning after recapture, the positional identifier/marker 300 may be used to control the correct rotational and/or axial and/or tilted orientation. In addition, the positional identifier/marker 300 on the tip section 130 may particularly improve positioning to such an extent that less recapture and repositioning events are necessary, which reduces structural wear of the stent portion 210.

When the heart valve implant 200 is in its desired position, the stent portion 210 is released from the connector 140 and completely expanded to engage the native annulus tissue. The catheter 100 is then removed from the body.

LIST OF REFERENCE NUMERALS

100 Catheter
110 Inner shaft
111 First guidewire lumen
120 Outer shaft
121 Capsule
122 Tapered connection
130 Tip section
131 Tip
132 Second guidewire lumen
140 Connector
141 Recess
200 Heart valve implant
210 Stent portion
220 Connecting element
230 Valve leaflet
300 Marker
301
302
First element
Second element
303 Third element
304 Fourth element
305 Fifth element
306 Gap D Distal end L Longitudinal axis With the context of the invention, the expression "geometric shape" denotes a geometric two-dimensional structure/shape which remains when location, scale, orientation and reflection are removed from the description of a geometric object. That is, the result of moving a shape around, enlarging it, rotating it, or reflecting it in a mirror is the same shape as the original, and not a distinct shape. With this context, structures that have the same shape as each other are said to be similar. If they also have the same scale as each other, they are said to be congruent.

With the above context, many two-dimensional geometric shapes can be defined by a set of points or vertices and lines connecting the points in a closed chain, as well as the resulting interior points. Such shapes are called polygons and include inter alia triangles, squares, and pentagons. Other shapes may be bounded by curves such as the circle or the ellipse.

In some embodiments, the first (301), the second (302), and the third geometric shape (303) may be either all similar (e.g. all lines), or all different (e.g. a line, a dot and a triangle), or may be two of them are similar (e.g. two lines) and the other one is different therefrom (e.g. a dot).

Thus, for instance, the first geometric shape may be selected from a line, a dot, an arrow-like shape, a circular shape, an elliptic shape or a polygon including a triangle, a square, and a pentagon, but not limited thereto.

The second geometric shape may be selected from a line, a dot, an arrow-like shape, a circular shape, an elliptic shape or a polygon including a triangle, a square, and a pentagon, but not limited thereto.

With the context of the invention, any suitable combination of the above described first, second and third geometric shape is disclosed herein for the skilled person provided that they allow for an adequate positioning of a medical implant in terms of its rotation and/or axial and/or tilted orientation in a human or animal body (e.g. a suitable combination of three lines).

The first geometric shape may be a line and the second geometric shape may be another line different from the first line, e.g. in terms of its orientation and/or length etc.

The first geometric shape may be a line and the second geometric shape may be an arrow-like shape, or vice versa.

The first geometric shape may be a dot and the second geometric shape may be a line, or vice versa.

In view the foregoing disclosure, the skilled person is well aware that a medical implant such as an artificial aortic heart valve may be held in a compressed state by an outer shaft/outer sleeve either itself or that is optionally connected to a distal capsule structure to keep the implant in a compressed/crimped state. Thus, in one embodiment, the catheter in accordance with the invention further includes and outer shaft optionally connected at a distal end thereof with a capsule structure.

In view of the foregoing disclosure, the visually so determined rotational orientation and/or axial orientation and/or tilted orientation of the tip section (130) relative to the surrounding tissue in accordance with the invention allows a physician to draw conclusions for the respective rotational orientation and/or axial orientation and/or tilted orientation of the medical implant (200) relative to its surrounding tissue; e.g. of an artificial aortic heart valve.

The invention claimed is:

1. A catheter for a medical implant that comprises a frame structure that requires an axial alignment, a rotational alignment and tilted alignment in a human or animal body, the catheter comprising:

- an inner shaft extending along a longitudinal axis (L), wherein the inner shaft is configured to receive the frame structure such that the frame structure is rotationally fixed to the inner shaft with respect to a rotation around the longitudinal axis (L), and
- a tip section connected to the inner shaft, wherein the tip section forms a distal end of the catheter, and wherein the tip section is rotationally fixed to the inner shaft with respect to a rotation around the longitudinal axis (L), wherein
  - the tip section that forms the distal end of the catheter comprises a positional identifier shaped and/or arranged such that a rotational orientation, an axial orientation, and a tilted orientation of the tip section relative to the surrounding tissue is discernable from the position and orientation of the positional identifier, wherein the positional identifier comprises portions that extend in different directions.

2. The catheter according to claim 1, wherein the positional identifier comprises a first element and a second element arranged with respect to each other such that the rotational orientation, the axial rotation, and the tilted orientation of the tip section relative to the surrounding tissue is discernable.

3. The catheter according to claim 2, wherein the first element extends in an axial direction with respect to the longitudinal axis (L) and the second element extends in a radial or circumferential direction with respect to the longitudinal axis (L).

4. The catheter according to claim 2 wherein the positional identifier comprises a third element that is perpendicular to the first element and/or the second element.

5. The catheter according to claim 4, wherein the first element comprises a first geometric shape, the second element comprises a second geometric shape, and the third element comprises a third geometric shape when viewed from the tip section in the direction of the longitudinal axis (L) or in a plane arranged perpendicular to the longitudinal axis (L).

6. The catheter according to claim 2, wherein the first element comprises a notch, and wherein the second element is arrangeable in the notch when viewed from the tip section in the direction of the longitudinal axis (L) or in a plane arranged perpendicular to the longitudinal axis (L), such that a rotational orientation and/or an axial orientation and/or a tilted orientation of the tip section relative to the surrounding tissue is discernable.

7. The catheter according to claim 1, wherein the positional identifier is shaped as a Latin letter selected from a group consisting of the letter B, the letter H, the letter L, the letter T, or the letter V, the Latin letter being visible when viewed in a direction perpendicular to the longitudinal axis (L) or in a plane parallel to the longitudinal axis (L).

8. The catheter according to claim 1, wherein the tip section comprises or consists of a radiotransparent material, and wherein the positional identifier comprises or consists of a radiopaque material.

9. The catheter according to claim 8, wherein the radiopaque material is barium sulphate ($BaSO_4$).

10. The catheter according to claim 1, wherein the tip section comprises or consists of a radiopaque material, and wherein the positional identifier comprises or consists of a radiotransparent material or is formed by a recess in the radiopaque material of the tip section.

11. The catheter according to claim 1, wherein the tip section and the position identifier comprises a radiopaque material at different concentrations to provide a radiographic contrast.

12. The catheter according to claim 1, wherein the tip section comprises or consists of a first radiopaque material and the positional identifier comprises or consists of a second radiopaque material different from the first radiopaque material, and wherein the second radiopaque material exhibits a radiographic contrast to the first radiopaque material.

13. The catheter according to claim 1, wherein the positional identifier is arranged on the surface of the tip section.

14. The catheter according to claim 1, wherein the positional identifier is embedded within the tip section.

15. The catheter according to claim 1, wherein the catheter comprises a connector for fixing the frame structure to the catheter, wherein the connector is rotationally fixed to the inner shaft with respect to a rotation around the longitudinal axis (L).

16. The catheter according to claim 15, wherein the connector comprises a plurality of recesses or protrusions, wherein the recesses or protrusions are configured to receive respective connecting elements of the frame structure to fix the frame structure to the catheter.

17. A catheter for a medical implant that comprises a frame structure that requires an axial alignment and a rotational alignment, the catheter comprising:

an inner shaft and an outer shaft arranged concentrically around the inner shaft;

a conical tip section connected to a distal end of the inner shaft, the conical tip section being formed from a smooth atraumatic material;

a heart valve implant on a distal portion of the inner shaft, the distal portion of the inner shaft being configured to receive a stent portion of the heart valve implant in a radially compressed configuration;

a capsule over the stent portion of the heart valve implant, the capsule being retractable in a proximal direction relative to the inner shaft to deploy the heart valve implant and being movable in a distal direction to recapture the heart valve implant when the heart valve implant is in a partially deployed condition; and a positional identifier in the conical tip section, wherein:

the positional identifier is shaped such that a rotational orientation of the conical tip section relative to the surrounding tissue is discernable from the orientation of the positional identifier;

the heart valve implant is rotationally fixed with respect to the inner shaft in a retracted or the partially deployed condition; and wherein the conical tip section is rotationally fixed to the distal end of the inner shaft.

18. The catheter according to claim 17, wherein the positional identifier is shaped as a Latin letter selected from a group consisting of the letter B, the letter H, the letter L, the letter T, or the letter V, the Latin letter being visible when viewed in a direction perpendicular to the longitudinal axis (L) or in a plane parallel to the longitudinal axis (L).

19. A catheter for a medical implant that comprises a frame structure that requires an axial alignment and a rotational alignment, the catheter comprising:

an inner shaft and an outer shaft arranged concentrically around the inner shaft;

a conical tip section connected to a distal end of the inner shaft, the conical tip section being formed from a smooth atraumatic material;

a heart valve implant on a distal portion of the inner shaft, the distal portion of the inner shaft being configured to receive a stent portion of the heart valve implant in a radially compressed configuration;

a positional identifier in the conical tip section, wherein:

the outer shaft extends over the stent portion of the heart valve implant, the outer shaft being retractable in a proximal direction relative to the inner shaft to deploy the heart valve implant and being movable in a distal direction to recapture the heart valve implant when the heart valve implant is in a partially deployed condition;

the positional identifier is shaped such that a rotational orientation of the conical tip section relative to the surrounding tissue is discernable from the orientation of the positional identifier;

the heart valve implant is rotationally fixed with respect to the inner shaft in a retracted or the partially deployed condition; and wherein the conical tip section is rotationally fixed to the distal end of the inner shaft.

20. The catheter according to claim 19, wherein the positional identifier is shaped as a Latin letter selected from a group consisting of the letter B, the letter H, the letter L, the letter T, or the letter V, the Latin letter being visible when viewed in a direction perpendicular to the longitudinal axis (L) or in a plane parallel to the longitudinal axis (L).

* * * * *